United States Patent
Hansen et al.

(10) Patent No.: US 6,227,853 B1
(45) Date of Patent: May 8, 2001

(54) MAGNETIC COUPLING SYSTEM AND METHOD

(75) Inventors: Thomas T. Hansen, Ames; Billy R. Flowers, Marshalltown, both of IA (US)

(73) Assignee: Edge Technologies, Inc., Ames, IA (US)

(*) Notice: Subject to any disclaimer, the term of this patent is extended or adjusted under 35 U.S.C. 154(b) by 0 days.

(21) Appl. No.: 09/354,611

(22) Filed: Jul. 16, 1999

Related U.S. Application Data

(60) Provisional application No. 60/119,661, filed on Feb. 11, 1999.

(51) Int. Cl.[7] ............................................... A61C 1/07
(52) U.S. Cl. ........................ 433/119; 433/147; 279/128
(58) Field of Search ............................... 433/119, 142, 433/143, 147, 86; 403/DIG. 1; 601/2; 279/128

(56) References Cited

U.S. PATENT DOCUMENTS

| | | | |
|---|---|---|---|
| 2,828,131 | * 3/1958 | Appleby | 279/128 |
| 2,912,249 | * 11/1959 | Eckold | 279/128 |
| 3,007,504 | * 11/1961 | Clark | 279/128 |
| 3,256,043 | * 6/1966 | Krekeler | 279/128 |
| 3,703,037 | 11/1972 | Robinson . | |
| 3,827,149 | 8/1974 | Brennan . | |
| 3,970,407 | * 7/1976 | Uffman | 279/128 |
| 4,080,737 | 3/1978 | Fleer . | |
| 4,207,485 | 6/1980 | Silver | 310/104 |
| 4,406,621 | 9/1983 | Bailey . | |
| 4,482,034 | 11/1984 | Baermann . | |
| 4,482,829 | 11/1984 | Tardieu et al. . | |
| 4,486,176 | 12/1984 | Tardieu et al. . | |
| 4,515,564 | 5/1985 | Lohn . | |
| 4,964,839 | 10/1990 | Gloor . | |
| 4,995,768 | * 2/1991 | Craft | 279/128 |
| 5,013,241 | 5/1991 | von Gutfeld et al. . | |
| 5,219,285 | 6/1993 | Meller et al. . | |
| 5,263,218 | 11/1993 | Giuliani et al. | 15/22.1 |
| 5,382,162 | 1/1995 | Sharp | 433/116 |
| 5,451,161 | 9/1995 | Sharp . | |
| 5,567,153 | 10/1996 | Foulkes et al. | 433/119 |
| 5,865,970 | 2/1999 | Stelter . | |
| 5,886,609 | 3/1999 | Stelter . | |
| 5,915,965 | * 6/1999 | Uffman | 433/118 |
| 5,921,562 | * 7/1999 | Robinson | 279/128 |

OTHER PUBLICATIONS

Moskowitz, L.R., "Classification of Permanent Magnets and Materials", *Permanent Magnet Design and Application Handbook, Second Edition*, Krieger Publishing Company, Malabar, Florida, 11–179, (1995).

* cited by examiner

*Primary Examiner*—Todd E. Manahan
(74) *Attorney, Agent, or Firm*—Schwegman, Lundberg, Woessner & Kluth, P.A.

(57) ABSTRACT

A magnetic coupling system comprising a magnetic assembly for removably combing a base structure and a tool insert is described. This arrangement allows energy from a transducer located in the base structure to be transmitted through the magnetic assembly to the tool insert. In one embodiment, the magnetic assembly comprises one or more magnetic inserts located between the base structure and tool insert and a permanent magnet or an electromagnet located proximate to the one or more magnetic inserts. The permanent magnet can be axially polarized, radially polarized or polarized at any intermediate angle. In one embodiment, the two components being coupled are a wave guide in direct contact with an ultrasonic motor and a dental scaling tool. In this embodiment, vibrational motion is transferred from the acoustic extension to the tool insert.

51 Claims, 12 Drawing Sheets

MAGNETIC COUPLING SYSTEM AND METHOD

This application claims the benefit under 35 U.S.C. 119 (e) of U.S. Provisional Application No. 60/119,661 filed on Feb. 11, 1999.

FIELD

This invention relates generally to coupling systems, and in particular the present invention relates to detachable coupling systems.

BACKGROUND

Coupling mechanisms or systems are used in a variety of devices to join various types of tools, such as drill bits, dental implements, etc., to a base structure, such as a transducer. Some coupling systems are also used to transmit torque from one component to another. Many of these coupling systems are intended to be relatively permanent, such that the joints are welded or soldered, as with hot plate welding and ultrasonic assembly. However, this type of arrangement lacks flexibility, since the user does not have the ability to use the same base structure with other tools. Further, since replacement of the tool also includes replacement of the base structure, this type of coupling system can be costly.

Detachable coupling systems, such as screw threads or latches, are designed to removably combine components. However, such designs can lead to galling or thread wear. Known detachable coupling systems which are magnetic are often relatively complex in their design and are typically used to transmit or resist torque. In the dental field, the coupling of sonic energy from a transducer to a liquid stream using a magnetostrictive rod is known, although due to the poor acoustic impedance match between solid and liquids, such transmission is relatively poor, or less than about 20%.

Therefore, what is needed is a simple detachable coupling system that efficiently transmits energy from a transducer to an attached tool.

SUMMARY

A magnetic coupling system comprising a magnetic assembly for removably combing a base structure and a tool insert is described. This arrangement allows energy from a transducer located in the base structure to be transmitted through the magnetic assembly to the tool insert. In one embodiment, the magnetic assembly comprises one or more magnetic inserts located between the base structure and tool insert and a permanent magnet or an electromagnet located proximate to the one or more magnetic inserts.

The permanent magnet can be polarized in any suitable manner, such as axially or radially or at any intermediate angle. In one embodiment, the permanent magnet or electromagnet is cylindrical in shape and surrounds the one or more magnetic inserts. In another embodiment, the permanent magnet is located between two magnetic inserts.

In an exemplary embodiment, the two components being coupled are a wave guide in direct contact with an ultrasonic motor and a dental scaling tool. In this embodiment, vibrational motion is transferred by the magnetic coupling system from the wave guide to the tool insert. If desired, the components are arranged such that the vibrational motion is transformed to flexural or elliptical motion at the tip of the tool insert.

The magnetic coupling system transfers energy efficiently and provides a firm connection during use. It gives the user the ability to quickly remove and attach implements as needed. The system is simple, inexpensive, and provides reliability by eliminating problems such as galling and thread wear.

DETAILED DESCRIPTION

In the following detailed description, reference is made to the accompanying drawings which form a part hereof, and in which is shown by way of illustration specific embodiments in which the inventions may be practiced. These embodiments are described in sufficient detail to enable those skilled in the art to practice the invention, and it is to be understood that other embodiments may be utilized and that mechanical, procedural, electrical and other changes may be made without departing from the spirit and scope of the present inventions. The following detailed description is, therefore, not to be taken in a limiting sense, and the scope of the present invention is defined only by the appended claims, along with the full scope of equivalents to which such claims are entitled.

The system described herein provides means for mechanically coupling two components together using a magnetic assembly. The magnetic assembly holds the two components firmly together in the presence of a magnetic field so that energy, such as kinetic energy, can be passed from one component to the other. The magnetic means can be used with various transducers, such as ultrasonic or sonic motors, and a variety of tools, such as dental ultrasonic scalers.

Figure 1A:
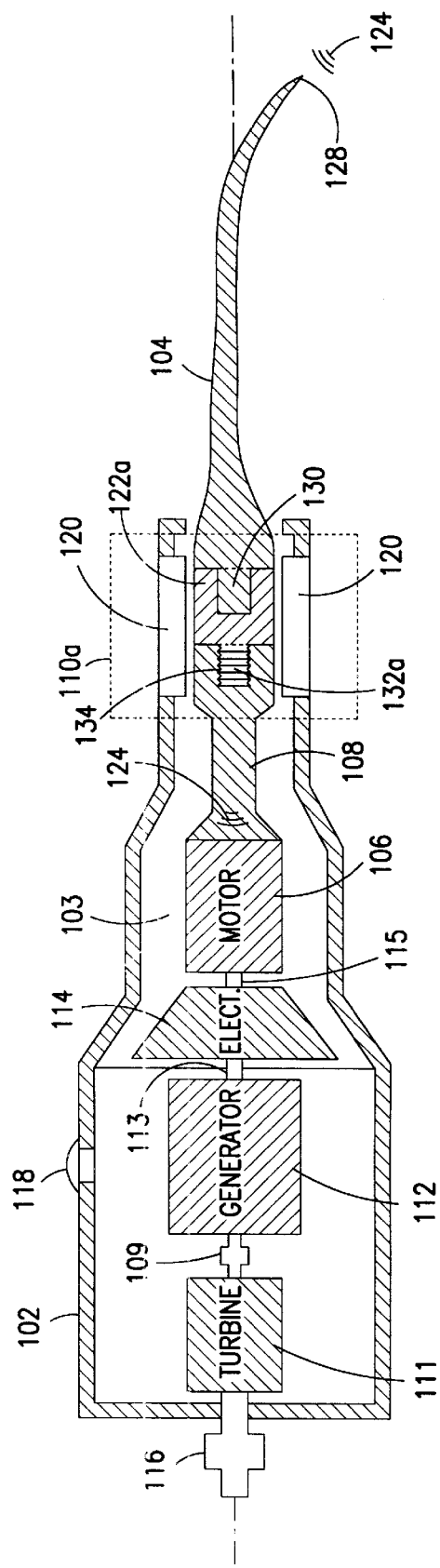
FIG. 1A is a cross-sectional view of a dental tool with a magnetic coupling system having a cylindrical permanent magnet in one embodiment of the present invention.

FIG. 1A shows a cross-sectional view of one embodiment of the present invention comprising a magnetic coupling system 110a within a handpiece 102 (having a handpiece cavity 103) which is coupled to a tool insert 104. The handpiece cavity 103 contains a motor 106, a wave guide 108 and the magnetic coupling system 110a The handpiece 102 also contains a turbine 111, a generator 112 and electronics 114, which are discussed further in FIG. 10. A turbine-generator connector 109 is located between the turbine 111 and generator 112, a generator-electronics connector 113 is located between the generator and the electronics 114, and a electronics-motor connector 115 can be located between the electronics 114 and the motor 106. In an alternative embodiment, there is no electronics-motor connector 115, and the electronics 114 and motor 106 are integral with each other or are otherwise modified to be directly connected. An air connector 116 as is known in the art is connected to the handpiece and a conventional power adjustment switch 118 is located on top of the handpiece 102. In the embodiment shown in FIG. 1A, the magnetic coupling system 110a comprises a permanent magnet 120 and an open-ended magnetic insert 122a.

The handpiece 102 can be any conventional handpiece designed for a particular application. In the embodiment shown in FIG. 1A, the handpiece 102 encloses the handpiece cavity 103 which contains all of the components located between, and including the turbine 111 and the magnetic coupling system 110a. In an alternative embodiment, the magnetic coupling system 110a extends beyond the end of the handpiece 102. The handpiece 102 can be made from any suitable material. In one embodiment, the handpiece 102 is made from plastic. In another embodiment, a hard plastic known as Ultem™ made by GE Plastics in Pittsfield, Mass. is used.

The magnetic coupling system 110a is used to detachably couple two mating parts and to transfer energy from one of the mating parts to the other. In the embodiment shown in FIG. 1A, the "mating parts" are the wave guide 108 and the tool insert 104. The wave guide 108 is an acoustic extension which transmits sound waves produced by the motor 106. In one embodiment, the wave guide 108 increases the amplitude of these sounds waves, and as such, can also be referred to as a "horn." The tool insert 104 is essentially a horn which is coupled to the wave guide 108 at one end, transferring energy to the tip 128 of the tool insert 104. (The term "horn" is generally understood in the art to be a component used to increase the amplitude of sound waves, such that both the wave guide 108 and tool insert 104 can be considered "horns" in certain embodiments. For clarity, however, the terms "wave guide" and "tool insert" will be used throughout this application to refer specifically to components 108 and 104, respectively).

The wave guide 108 and tool insert 104 can both be made from any suitable material, but do not necessarily need to be made of the same material. It is known that the speed at which sound travels through a material is related to several factors including, but not limited to, its temperature, modulus of elasticity, density, Poisson's ratio, and so forth. In one embodiment the material used for the wave guide 108 and tool insert 104 is a very low damping (high quality factor {Q}) nonmagnetic material, although the invention is not necessarily so limited. The damping capacity of a material decreases in accordance with decreasing elastic hysteresis. As a result, materials with low elastic hysteresis, or materials having a relatively low density, such as aluminum, magnesium or titanium, with densities of about 1.8 to 4.8 gram/cubic centimeter (g/cc), demonstrate a relatively high vibration amplitude output velocity, which can be expressed as a vibration output of one unit of displacement. Conversely, and in accordance with the conservation of momentum principle, high density materials, such as stainless steel and tungsten, having densities of about 7.5 to 18.5 g/cc, limit the net amplitude which can be produced by a component, such that the transfer of vibrations through the material is decreased to about one-fifth to one-half unit of displacement.

Since velocity is proportional to frequency times amplitude, the actual velocity or vibration output is also dependent on the type of motor used. Therefore, for a given motor frequency, when the density of the wave guide material is doubled, the velocity of the output for the wave guide 108 is typically reduced by about one-half. In one embodiment, the density of the material used for the wave guide 108 and tool insert 104 is about four (4) to 4.8 g/cc. In another embodiment, the material has a "Q" greater than about 100 and a fatigue strength ranging from about 12,420 to 96,600 MPa (about 18,000 to 140,000 psi).

Examples of materials which can be used include, but are not limited to, acoustic metals such as aluminum, magnesium, titanium and alloys of these metals. This includes materials which are of various American Society for Testing and Materials (ASTM) types as described on page 9 in U.S. application Ser. No. 08/855,228 (hereinafter "U.S. application") filed on May 13, 1997 and owned by the same Assignee as this application, which is hereby incorporated by reference in its entirety. (See also PCT International Patent Application No. PCT/US98/09848 (hereinafter "PCT Application") deposited on May 11, 1998 and also owned by the same Assignee as this application, which is hereby incorporated by reference in its entirety).

The wave guide 108 and tool insert 104 can also be made from magnetic materials. In one embodiment, any of the approximately 70 standard types of ferromagnetic stainless steel or steel alloys are used. These steels are produced in "wrought form" American Iron and Steel Institute (AISI) types and as "cast alloy" Alloy Casting Institute (ACI) types. Generally, all of these materials are iron-based, although some, such as the 300 series stainless steel, are so low in iron as to be considered non-magnetic. These steels or steel alloys also contain about 12 to 30 percent chromium, about zero (0) to 22 percent nickel, and minor amounts of carbon, columbium, copper, molybdenum, selenium, tantalum and titanium. Examples of materials which can be used include, but are not limited to 420 stainless steel, 18-4 stainless steel, 17-4 PH precipitation-hardening stainless steel, and so forth. In another embodiment, carbon steels and certain nickel-based alloy steels are used. A steel wave guide 108 may be preferable in powder metallurgy applications where work is being performed on very stiff, high acoustic impedance materials, such as tungsten. In another embodiment, the wave guide 108 is made from a nonmagnetic material as described above and the tool insert 104 is made from a magnetic material. In a specific embodiment, the wave guide 108 is made from titanium and the tool insert 104 is a dental tool made from 420 stainless steel.

As noted above, the wave guide 108 transmits sounds waves from a transducer, such as a motor. In the embodiment shown in FIG. 1A, the wave guide 108 interacts directly with the motor 106 and transmits energy from the motor 106 to the tool insert 104. In one embodiment, vibrations 124, i.e., vibrational motion, is transferred through the wave guide 108 and across the magnetic coupling system 110a to the tip 128 of the tool insert 104 as shown. Vibrational motion can also be transformed to flexural or elliptical motion at the tip 128, when the tool insert 104 is aligned off-center in relation to the other components. Such motion can be desirable for certain applications with a dental scaler, for example. In an alternative embodiment, a non-steady or pulsing energy is transferred. In yet another alternative embodiment, more than one wave guide 108 is used. However, adding additional wave guides 108 can cause additional power losses, and at some point, it is not efficient or practical to add more wave guides 108. In one embodiment, two (2) to four (4) wave guides 108 are used. In an alternative embodiment, there is no wave guide 108, and the motor 106 transmits energy through the magnetic coupling system 110a to the tool insert 104.

The wave guide 108 can be any suitable size and shape depending on the particular application. For example, in the embodiment shown in FIG. 1A, the wave guide 108 is intended to be part of a hand held tool, and is designed to be a convenient and comfortable size for performing detailed work. In one embodiment, the wave guide 108 is about one-half the size of the tool insert 104. The size of the wave guide 108 is also dependent on the desired frequency being generated by the motor 106. In general, the higher the frequency, the smaller the length of wave guide 108 which is required. In one embodiment, the wave guide is about 0.4 to 1.7 cm (about 0.16 to 0.7 in) in diameter and about 2.5 to ten (10) cm (about one (1) to 3.9 in) in length. In a particular embodiment, the wave guide 108 is about five (5) cm (about two (2) in) long.

In an alternative embodiment, the diameter of the wave guide 108 is larger than about 1.9 cm (about 0.75 in) up to about nine (9) cm (about 3.5 in) or more in diameter or length. When the diameter of the wave guide 108 is large, such as greater than about nine (9) cm (about 3.5 in), side motion and transient frequencies can alter the amplitude at the interface of the tool insert 104 and create internal stress. A wave guide 108 of this size may be needed when the tool insert 104 has a large diameter. In one embodiment, one or more suitably-designed slots are machined into the sides of the wave guide 108. The use of slots effectively divides the wave guide 108 into smaller, individual wave guides 108, ensuring uniform amplitude and relieving internal stresses, thus reducing transverse vibrations. Large wave guides 108 can also be used with a motor 106 having a power output of about 25 kW or more.

The wave guide 108 and motor 106 can be coupled together in any suitable way. In one embodiment, the wave guide 108 is a solid, cylindrically-shaped object which can be designed to fit together with other components as needed. In the embodiment shown in FIG. 1A, the cylindrically-shaped wave guide 108 flares out at the end adjacent to the motor to be contiguous with the motor 106. In a particular embodiment, the wave guide 108 and motor 106 are manufactured as one unit. In an alternative embodiment, the wave guide 108 does not flare out at the motor end, but is still contiguous with the motor 106. In another alternative embodiment, the wave guide 108 is connected to the motor in any suitable manner such as with threads, welding, press fitting, and so forth.

In the embodiment shown in FIG. 1A, the opposing or coupling end of the wave guide 108 also flares out, although this is not necessary for the invention, as long as the two mating parts (wave guide 108 and tool insert 104) can be adequately coupled together. Similarly, the exact size and shape of the tool insert 104 is not important, as long as the mating end of the tool insert 104 can be joined with the open-ended magnetic insert 122a or to the mating end of the wave guide 108, if no open-ended magnetic insert 122a is used. Depending on the particular design, a variety of tool inserts 104 can be used. In one embodiment, the tool insert 104 is any type of tool used to perform work such as a dental tool, knife blade, surgical instrument, chemical applicator, drill bit, and so forth. In the embodiment shown in FIG. 1A, the tool insert 104 is a dental scaler having a tip 128 on one end. The mating end of the tool insert 104 has a tool insert stub 130 and is essentially a "male" end which couples with the open-ended magnetic insert 122a as described below. In one embodiment, the tip 128 has a diameter of about 0.05 mm (0.002 in) and the tool insert stub 130 has a diameter of about 0.64 cm (0.25 in). In an alternative embodiment, the tool insert 104 has two or more tips 128. For example, a dental scaler can be combined with a lavage tip for dispensing water through or over the surface of the scaler tip.

As noted above, the magnetic coupling system 110a shown in FIG. 1A comprises one open-ended magnetic insert 122a and the permanent magnet 120, although the design is not so limited. Any suitable number and type of magnetic insert can be used, and does not necessarily need to be open-ended on one end. The magnetic insert can have two open ends or can have two stubs as described in FIG. 2. Typically, one magnetic insert is used when one of the mating parts, i.e., the wave guide 108 or tool insert 104, is nonmagnetic. Two or more magnetic inserts are typically used if both mating parts are nonmagnetic. In an alternative embodiment, both mating parts are magnetic and no magnetic inserts are used.

Figure 1B:
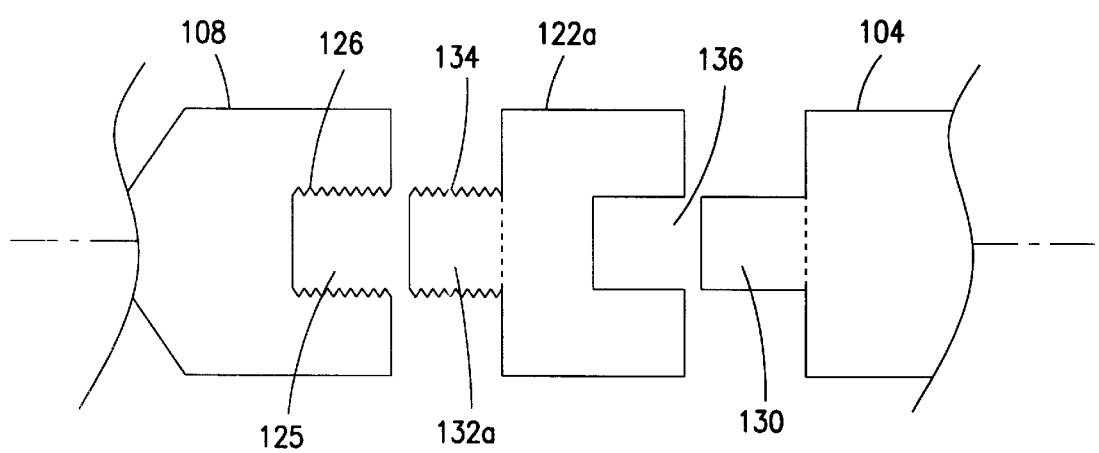
FIG. 1B is an enlarged cross-sectional partial view of a magnetic insert in between two mating parts in one embodiment of the present invention.

In the embodiment shown in FIG. 1A, the open-ended magnetic insert 122a has a "male" end and an opposing "female" end. The "male" end, or magnetic insert stub 132a, has stub threads 134 and is designed to couple with the wave guide cavity 125 which has wave guide cavity threads 126 located around its circumference, as shown in FIG. 1B. Similarly, the opposing "female" end of the open-ended magnetic insert 122a forms a magnetic insert cavity 136 as shown in FIG. 1B and is designed to couple with a male component, such as the tool insert stub 130. Any suitable tolerance between the magnetic insert cavity 136 and the male component can be used, such as about 0.025 mm to 0.125 mm (about 0.001 to about 0.005 in).

The wave guide 108, open-ended magnetic insert 122a and tool insert 104 are joined together by inserting the magnetic insert stub 132a into the wave guide cavity 125 and screwing the two components together. The tool insert stub 130 is inserted, but not screwed, into the open end of the open-ended magnetic insert 122a, i.e., the magnetic insert cavity 136. When combined with the use of an attractive magnetic force as provided by the permanent magnet 120, such an arrangement provides a firm connection between the components, as shown in FIG. 1A, and reduces or eliminates sliding of the components perpendicular to the axial direction.

In an alternative embodiment, neither the wave guide cavity 125 nor the magnetic insert stub 132a has threads, and the magnetic insert stub 132a is press fit into the wave guide cavity 125. Press fitting may require heating the end of the wave guide 102 with the wave guide cavity 125 to about 500 C and placing the magnetic insert stub 132a into liquid nitrogen or vice versa. Such a process results in a strong connection between the two components, but can be a relatively expensive procedure. In another alternative embodiment, the female end of the open-ended magnetic insert 122a, i.e., the magnetic insert cavity 136, has threads around its circumference for coupling with threads located on the tool insert stub 130. In this way, the tool insert stub 130 can be screwed into the open-ended magnetic insert 122a prior to the connection being enhanced with magnetics, i.e., the magnetic coupling system 110a.

Figure 2:
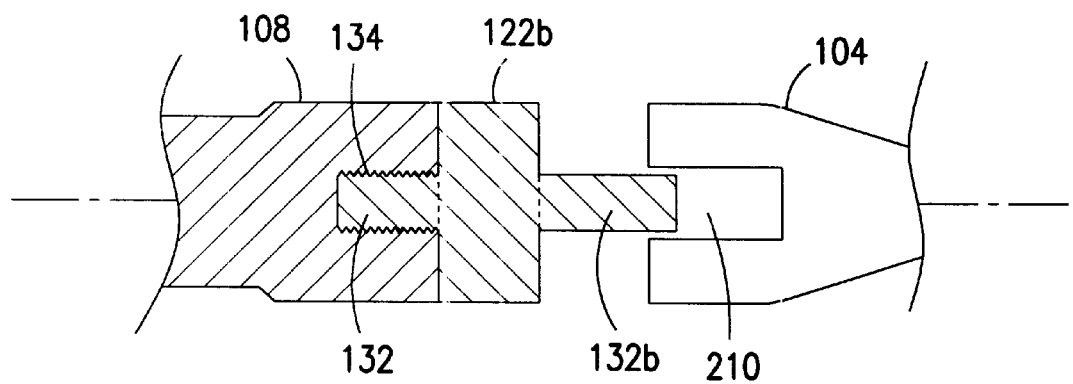
FIG. 2 is an enlarged cross-sectional partial view of an alternative magnetic insert in between two mating parts in one embodiment of the present invention.

In yet another alternative embodiment shown in FIG. 2, a dual-stubbed magnetic insert 122b is used. In this embodiment, the dual-stubbed magnetic insert 122b has the magnetic insert stub 132a as shown in FIGS. 1A and 1B. Rather than an opposing female end, however, the dual-stubbed magnetic insert 122b has an opposing magnetic insert stub 132b. In order to accommodate the opposing magnetic insert stub 132b, the tool insert 104 is also modified to have a female end or tool insert cavity 210 as shown in FIG. 2. The opposing magnetic insert stub 132b does not have any threads, and couples with the tool insert 104 by slipping into a tool insert cavity 210, with tolerances similar to those described in FIG. 1B. As shown in FIG. 2, opposing magnetic insert stub 132b can be slightly longer than magnetic insert stub 132a in order to provide a suitable amount of transverse stability to the tool insert 104. In one embodiment, the magnetic insert stub 132a extends about 0.1 to about 100 cm into the wave guide and the opposing magnetic insert stub 132b extends about 0.1 to about 150 cm into the tool insert 104. In an alternative embodiment, the opposing magnetic insert stub 132b is threaded and screws into suitable threads in the wave guide cavity 210. In another alternative embodiment, the magnetic insert stub 132a does not have magnetic insert threads 134, and is instead press fit into the wave guide cavity 125 as described above.

The magnetic insert(s) used in the magnetic coupling system 110a (or 110b or 110c described below) are essentially "flux catchers" or channels, and can be made from any suitable material which exhibits a net magnetization strong enough to hold the mating parts together during operation. Specifically, the material must have a suitable magnetic permeability, i.e., be able to pass or conduct lines of a magnetic force. In one embodiment, the permeability of the magnetic insert is about 50 to 5,000, up to about 100,000 or more. In one embodiment, the magnetic insert is ferromagnetic. A ferromagnetic material is a substance which has a high magnetic permeability, a definite saturation point, significant residual magnetism and low hysteresis. Ferromagnetic materials are typically characterized as either "hard" or "soft" materials. Permanent (or hard) magnets having a high coercivity of greater than about 100 to about 20,000 oersted (Oe) can be used as the magnetic insert. Temporary (or soft) magnets with a low coercivity of less than about 100 Oe can also be used, depending on the particular application.

In one embodiment, the magnetic insert comprises a soft ferromagnetic material, such as iron, amorphous iron alloys, amorphous cobalt alloys and permalloy. This includes, but is not limited to, iron-aluminum alloys containing about 12 to 16 percent aluminum. This also includes, but is not limited to, various soft ferrites and silicon steels, including nonoriented and grain-oriented steels having varying amounts of silicon from about 0.5 to about five (5) percent. Soft ferromagnetic materials further include, for example, iron-cobalt alloys having up to about 65 percent cobalt. It is known that such alloys have a higher magnetic saturation value than pure iron. In one embodiment, vanadium permendur, which contains about 49% cobalt, 49% iron and about two (2)% vanadium is used.

In another embodiment, the magnetic insert is a hard ferromagnetic material such as carbon steel, bonded rare earth materials, a class of copper-manganese-tin alloys known as "Heusler" alloys, tungsten steel, hard ferrites, neodymium-iron-boron materials and samarium-cobalt materials. This includes, but is not limited to, iron-nickel alloys which can have from about 25 to 60 percent nickel. Alloys containing about 30 percent nickel can also be used and are useful in magnetic circuits when temperature-related changes may occur. Other materials which can be used include certain alloys of cobalt, titanium, aluminum and nickel, commonly known as "alnico." This includes, for example, alnico 2, alnico 5 (Ticonal), alnico 5DG, alnico 6, alnico 9, alcomax II and alcomax m. In an alternative embodiment, barium oxide or strontium oxide magnets, i.e., ceramic magnets, are used. In another alternative embodiment, paramagnetic inserts made from materials such as aluminum, platinum, manganese and chromium, are used.

Referring again to FIG. 1A, the permanent magnet 120 can be embedded into or secured onto the handpiece 102 in any suitable manner. In one embodiment, an internal plastic or metal clip (not shown) is used to hold the permanent magnet 120 in place. In another embodiment, the permanent magnet 120 is permanently affixed to the handpiece 102 with any type of conventional adhesive. The permanent magnet 120 can be located in a suitable secondary cavity within the handpiece 102. The permanent magnet 120 can be any suitable shape and size. In the embodiment shown in FIG. 1A, the permanent magnet 120 is cylindrical, having an external diameter of about one (1) to about five (5) cm (about 0.4 to about two (2) in), a length of about one (1) to about 12 cm (about 0.4 to about 4.7 in) in length, and a thickness of about 0.1 to about ten (10) cm (about 0.4 to about four (4) in).

Figure 3:
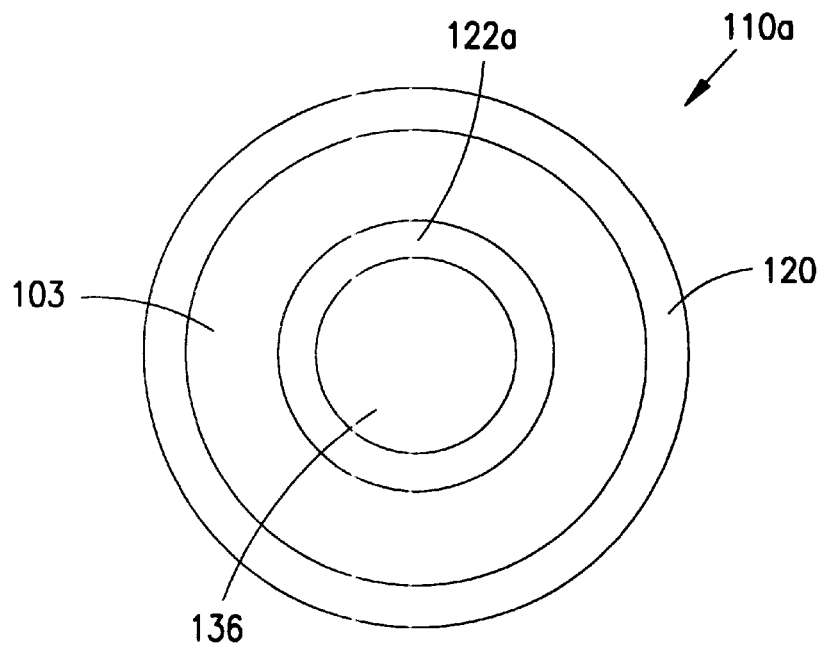
FIG. 3 is an end view of a magnetic coupling system in one embodiment of the present invention.

FIG. 3 is an end view of the magnetic coupling system 110a in FIG. 1A looking toward the magnetic insert cavity 136 (before the tool insert 104 is in place). As shown in FIG. 3, the cylindrical permanent magnet 120 surrounds the open-ended magnetic insert 122a which is located within the handpiece cavity 103 and connected to the wave guide 108 (not shown). The permanent magnet 120 can be made from any suitable hard magnetic material as discussed above. This includes various grades of neodymium iron boron, samarium cobalt, barium oxide, strontium oxide, and so forth. In one embodiment, the permanent magnetic materials described herein are manufactured according to current commercial standards, such as the standards and specifications established by The Magnetic Materials Producers Association (MMPA) in the "Standard Specifications for Permanent Magnet Materials," MMPA Standard No 0100-96, as reprinted on pages 188–788 of the "Permanent Magnet Design and Application Handbook," 2d edition, by L. Moskowitz, or any comparable or updated standards for permanent magnetic materials. In one embodiment, the permanent magnet 120 is shipped in a demagnetized state from the manufacturer, and is magnetized again after placement in the final magnetic circuit.

The general principles of magnet manufacturing as well as magnetism and permanent magnet design are well known in the art and are not discussed in detail herein. See, for example, Chapters 5–14 of Moskowitz, supra, which are hereby incorporated by reference in their entirety. Many factors can affect the performance of a magnet, including, but not limited to, magnet material, size, shape, and location of the magnet in the magnetic circuit, level of magnetization, location of magnetic poles, magnetization before or after placement in a final circuit, material from which other components are made, shape of the other components, temperature, radiation, shock, demagnetizing fields, physical handling during assembly, time, the material of the part on which the magnet acts, the size, shape and location of the part on which the magnet acts, and so forth. (See p. 40 of Moskowitz, supra).

Figure 4:
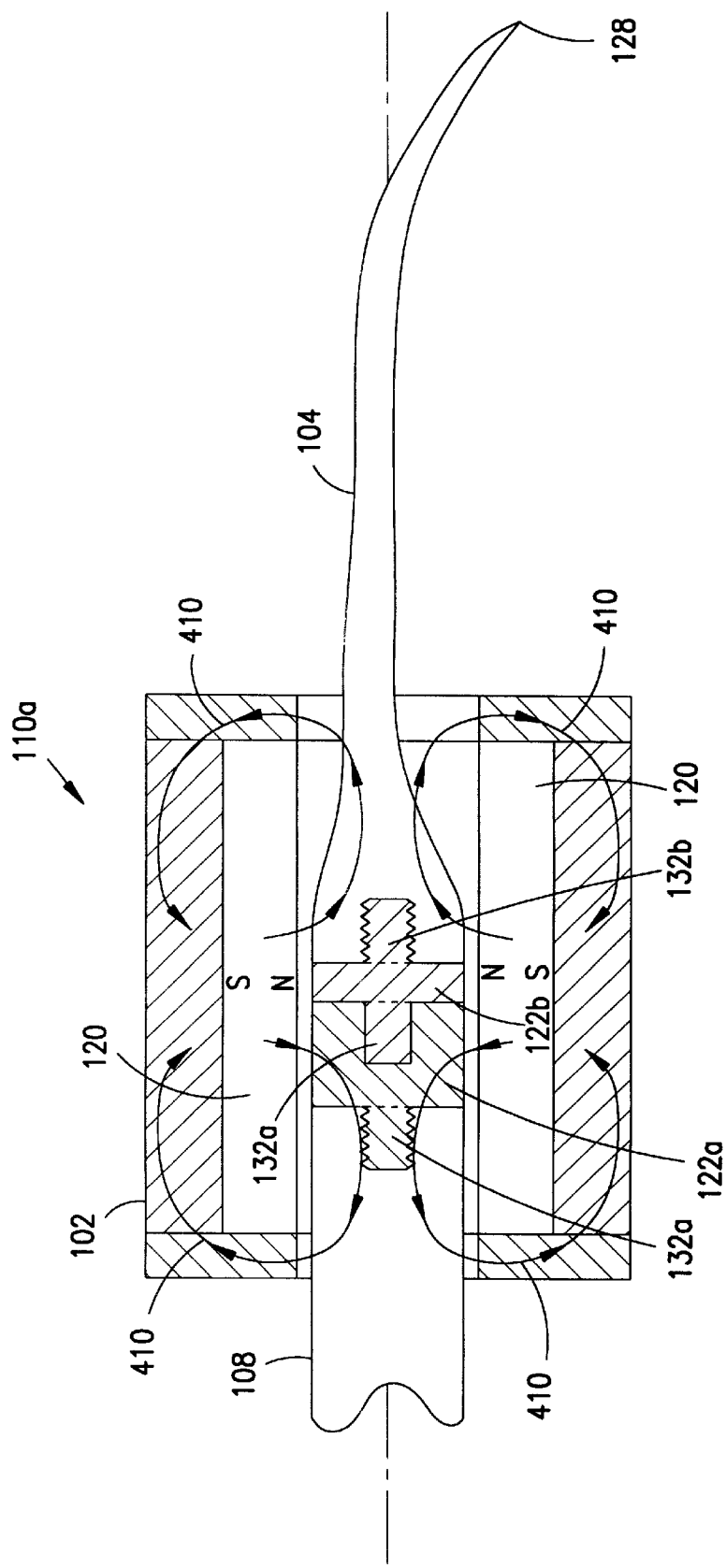
FIG. 4 is a cross-sectional partial view of a dental tool having a magnetic coupling system with a cylindrical permanent magnet which is radially polarized in one embodiment of the invention.
Figure 5A:
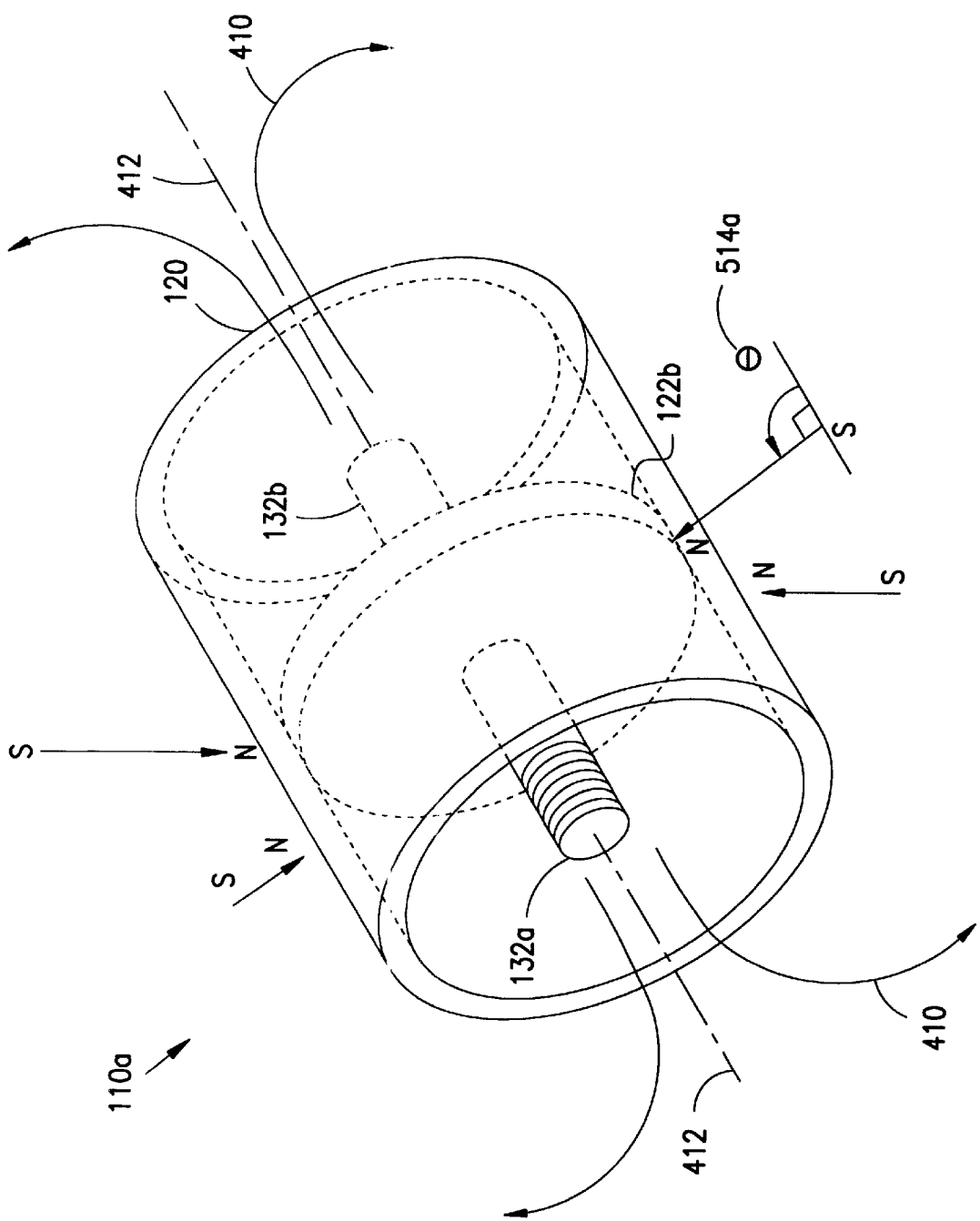
FIGS. 5A, 5B and 5C are simplified perspective illustrations of the magnetic coupling system shown in FIG. 1A with the corresponding flux lines showing radial polarization, axial polarization and intermediate radial polarization, respectively.
Figure 5B:
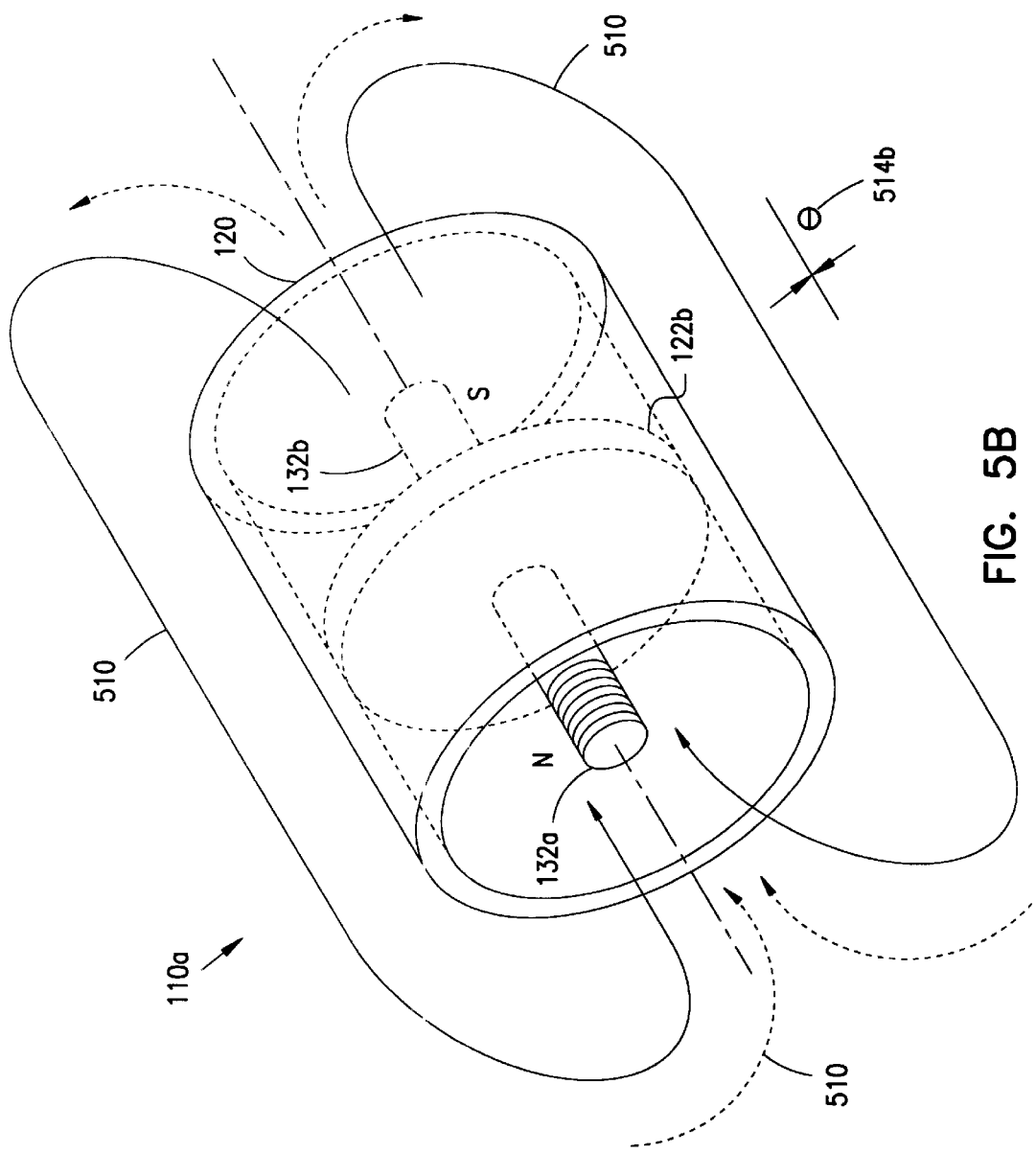
Figure 5C:
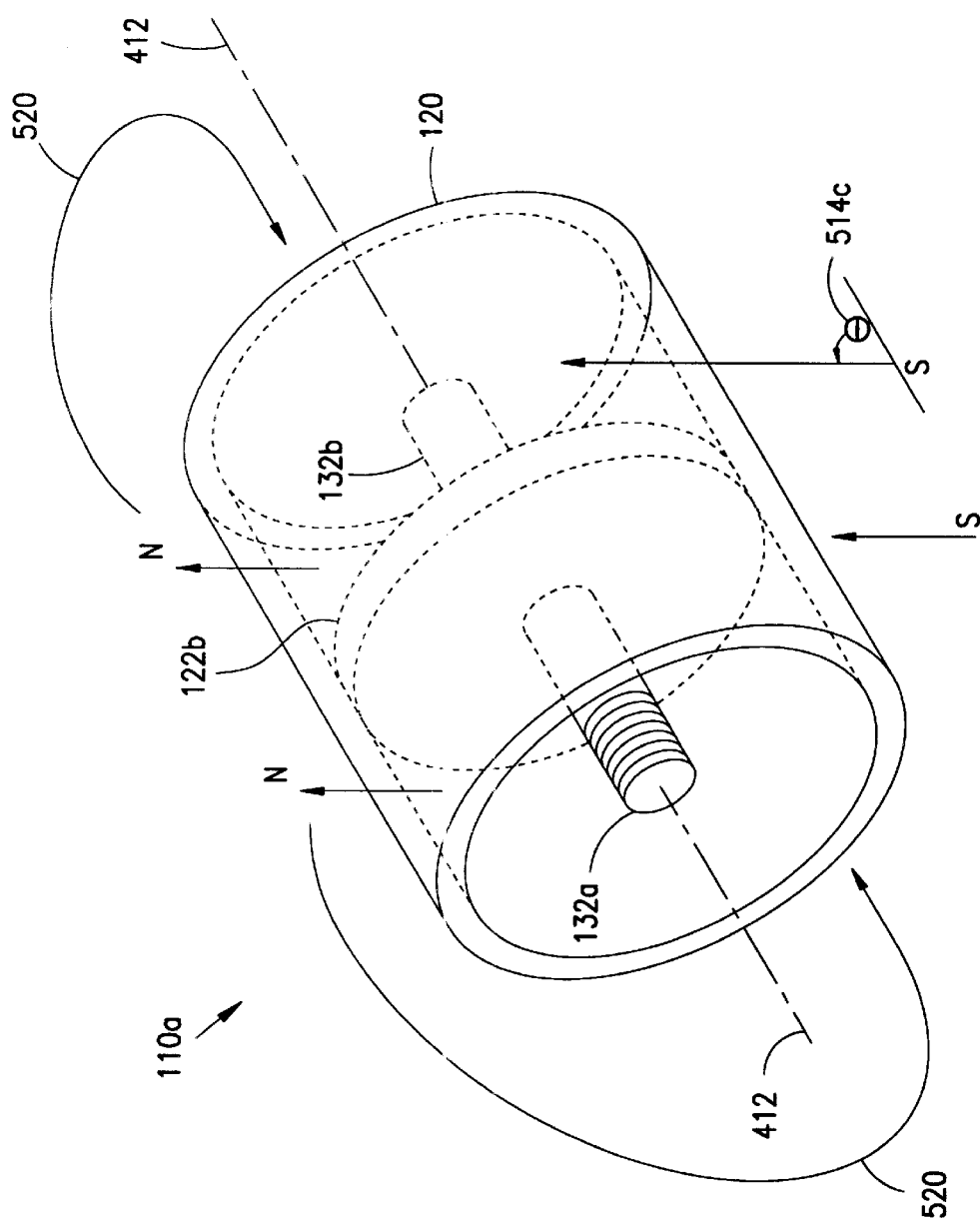

In the embodiment shown in FIG. 1A, the permanent magnet 120 is placed longitudinally in the cavity 103 such that the largest surface area of the permanent magnet 120 is pointed directly at the open-ended magnetic insert 122a. With this configuration, it is possible to use a permanent magnet 120 which has been manufactured to have any one of a number of different polarizations. Polarization is the primary direction toward which lines of magnetic flux vectors are pointing. In one embodiment, magnetic coupling is achieved by radial (90 degrees) polarization of the permanent magnet 120 relative to the centerline of the mating parts (FIGS. 4 and 5A). In another embodiment, magnetic coupling is achieved using axial (0 degrees) polarization of the permanent magnet 120 (FIG. 5B). In yet another embodiment, magnetic coupling is achieved using an intermediate angle (0–90 degrees) of polarization of the permanent magnet 120 (FIG. 5C). Use of such "off-axis" polarization (relative to the axial axis) may be advantageous in creating a larger magnetic force as compared with polarization along the axis. Therefore, the axial alignment of the permanent magnet 120 with the open-ended magnetic insert 122a (or double-stubbed magnetic insert 122b) can vary depending on the particular application and the amount of magnetic attraction desired.

FIG. 4 is a cross-sectional partial view of a dental tool having a magnetic coupling system 110a with a permanent magnet 120 which is radially polarized. In this embodiment, two magnetic inserts 122a and 122b are used. As noted above, two magnetic inserts are typically used when both the wave guide 108 and the tool insert 104 are non-magnetic. The open-ended magnetic insert 122a which couples with the wave guide 108 has been described above in FIGS. 1A and 1B. The dual-stubbed magnetic insert 122b which couples with the tool insert 104 is similar in design to the dual-stubbed magnetic insert 122b shown in FIG. 2. In this embodiment, however, the magnetic insert stub 132a is not threaded and the opposing magnetic insert stub 132b is threaded. The poles of the permanent magnet 120 are marked on the drawing by the letters "N" and "S," and are oriented such that all vectors or flux lines 410 point radially inwardly towards a centerline 412 as shown, passing through the open-ended magnetic insert 122a and the dual-stubbed magnetic insert 122b.

Similarly, FIG. 5A shows a perspective view of the magnetic coupling system 110a in which the permanent magnet 120 is radially magnetized. As with FIG. 4, flux lines 410 exit the permanent magnet 120 radially towards the centerline 412 at a 90 degree angle (θ) 514a relative to the longitudinal axis of the permanent magnet 120. Again, the flux lines 410 are directed radially inward before turning back across an air gap, which is generally defined as any nonmagnetic discontinuity in a magnetic circuit. (Although the poles and orientation of the dual-stubbed magnetic insert 122b are not noted on these drawings, it can be assumed that the dual-stubbed magnetic insert 122b is aligned such that it exerts a magnetic attraction at each end for each of the mating parts being combined).

FIG. 5B shows an alternative embodiment in which the magnetic coupling system 110a utilizes a permanent magnet 120 which is axially polarized. In this embodiment, the poles (N and S) of the permanent magnet 120 are located at opposite ends as shown, such that polarization is parallel to the axial axis of the dual-stubbed magnetic insert 122b. Specifically, flux lines 510 exit one end of the permanent magnet 120, curving back along the length of the permanent magnet 120, such that angle (θ) 514b is zero (0) degrees. The flux lines 510 are attracted toward the dual-stubbed magnetic insert 122b, causing them to curve back into an opposing end of the permanent magnet 120 toward the dual-stubbed magnetic insert 122b, as shown.

FIG. 5C shows another alternative embodiment in which the magnetic coupling system 110a utilizes a permanent magnet 120 which has an intermediate angle of polarization. In this embodiment, the poles (N and S) are located along the length of the permanent magnet 120 as shown. Flux lines 520 exit the permanent magnet 120 radially inward at an acute angle (θ) 514c relative to the longitudinal axis of the permanent magnet 120. The flux lines 520 then pass through the dual-stubbed magnetic insert 122b and return to the permanent magnet 120 as shown, such that the entire permanent magnet 120 is magnetized radially inwardly. In one embodiment, the angle (θ) 514c is any acute angle greater than zero (0) degrees. In another embodiment, the angle (θ) 514c is between about 30 and 60 degrees.

In one embodiment, soft magnetic materials are used to shape and intensify the magnetic flux density or magnetic field strength. In a particular embodiment, the magnetic flux density is doubled when magnetic material is placed on the outside of the permanent magnet 120 and has flux vectors pointed radially inward.

In another alternative embodiment (not shown), two or more permanent magnets 120 are used. In this embodiment, each permanent magnet 120 does not necessarily surround the magnetic insert (122a or 122b), but can be placed at suitable intervals around the interior circumference of the handpiece 102, so that the magnetic insert is effectively surrounded by a group of permanent magnets 120, each of which can have a solid core. In one embodiment, the permanent magnets 120 are arranged to reduce leaking and fringing flux. An overview of permanent magnet structures, including a discussion of leakage flux and fringing flux is provided in U.S. Pat. No. 5,886,609 to Stelter, which is hereby incorporated by reference in its entirety.

Referring again to FIG. 1A, the motor 106 can be any suitable type of motor having a drive rod capable of generating sufficient power for a particular application. In one embodiment, the drive rod is made from a smart or active material, such as a magnetostrictive, piezoelectric or piezoceramic material. A magnetostrictive material is known to tolerate high mechanical stress and have a relatively high energy density. In a particular embodiment, a drive rod made from a magnetostrictive material known as TERFENOL-D is used. TERFENOL-D is manufactured by the Assignee of this application, ETREMA Products, Inc. of Ames, Iowa. In one exemplary embodiment, a "High Power Ultrasonic Motor" as described in U.S. or PCT Applications, supra, is used. In a specific embodiment, a six (6) kW motor 106 having boron nitride parts is used.

In another embodiment, the high power ultrasonic motor as described in U.S. and PCT Applications, supra, may be modified in any suitable way as needed for a particular application. For example, a smaller or larger motor can be used. Alternatively, the power supply may be of the impulse or continuous type. In one embodiment, the motor 106 is cylindrical in shape and is less than about 7.6 cm (about three (3) in) in diameter and less than about 10.2 cm (about four (4) in) in length. In another embodiment, the motor 106 is at least about 1.3 cm (0.5 in) in diameter and about 2.5 cm (one (1) in) in length.

In an alternative embodiment, the motor 106 is smaller than the motors described in U.S. and PCT Applications, supra, because there are no separate cooling fixtures. The elimination of cooling fixtures is possible in applications where no additional cooling is needed, such as in the dental field, wherein fluid is actively passed through the motor 106 in order to provide irrigation during dental procedures. In such applications, a hole can be bored through the center of the motor 106, allowing the water or other cooling fluid to pass through the center bolt. Preload is provided by the bolt, rather than a Belleville spring, as in U.S. and PCT Applications, supra. Necessary adjustments can be made to the bolt to reduce its stiffness, so that it has the necessary softness similar to a Belleville spring. Cooling is also typically not needed in small motors consuming less than about ten (1) to 20 watts of power.

The motor 106 used with the magnetic coupling system 110*a* shown in FIG. 1A can operate at any suitable frequency. In one embodiment, the operating frequency is ultrasonic, such as between about 18 kHz and 100 kHz. In another embodiment, the motor 106 operates between about 25 kHz and about 40 kHz, such as with a dental tool and other similar devices. In yet another embodiment, frequencies below about 18 kHz are used. Frequencies below 25 kHz are more likely used for applications such as impact hammers, compaction equipment, and so forth.

Any suitable amount of power can be transmitted from the electronics 114 to the motor 106. In one embodiment, less than about ten (10) watts of power is transferred. In an alternative embodiment, about ten (10) to 20 watts or more of power is transferred from the electronics 114 to the motor 106. Further, any suitable amount of power can be output from the motor 106. In one embodiment, about 30 to 70% or more of the power input to the motor 106 is output by the motor 106 through the magnetic coupling system 110*a*. In another embodiment, about 40 to 50% is output. In a specific embodiment, about 13 watts of power is input from the electronics 114 to the motor 106 and about 5.8 to six (6) watts, i.e., about 46%, is output by the motor 106 through the magnetic coupling system 110*a*.

The magnetic coupling system 110*a* can transfer energy from the motor 106 to the tip 128 at any suitable efficiency. In one embodiment, the coupling efficiency of the magnetic coupling system 110*a* is about 30 to 50% up to about 60% or 70% or more, up to 100% of the power generated by the motor 106. The efficiency of the magnetic coupling system 110*a* can also be expressed in terms of the vibrational output or amplitude. For example, in one embodiment, an amplitude of about one (1) to 100 μm is generated in the wave guide 108 by the motor 106, and an amplitude of about 0.9 to 100 μm, i.e., about 90 to 100%, is output at the tip 128.

The size and shape of the tool insert 104 and the wave guide 108 can be varied depending on the frequency used and the type of function or work performed by the tool insert 104. As noted above, the wave guide 108 can be any length in relation to the tool insert 104, and in one embodiment, is about one-half the length of the tool insert 104. In such an embodiment, the wave guide 108 has about ¼ the wavelength of sound propagation in the material for any given frequency as compared with the tool insert 104. In one embodiment, a motor 106 having a frequency output of about 20 kHz is used together with a tool insert 104 having a diameter of about two (2) to three (3) cm (about 0.8 to 1.2 in) and a length of about ten (10) to 12 cm (about four (4) to 4.7 in). A wave guide 108 which is one-half the length of the tool insert, i.e., about five (5) to six (6) cm (about two (2) to 2.4 in), can be used, if desired. The amplitude of the displacement at the tip 128 can also vary depending on the application. In one embodiment, the displacement amplitude is about one (1) micron to about 300 microns. In another embodiment, the displacement amplitude is about 100 microns peak-to-peak.

Power can be provided from any suitable source of energy, including, but not limited to, a generator, conventional batteries, a solar energy system having solar panels and storage batteries, or a normal power grid system. The magnetic coupling system 110*a* can operate on either alternating current (AC) or direct current (DC), and the voltage can be any suitable voltage such as 12 volts or 120 volts, depending on the source of the power. In one embodiment, a battery pack system is used. In this embodiment, the battery pack supplies DC power to a conversion circuit. The conversion circuit converts the DC power to any desired frequency range, such as from about one (1) Hz to 50 kHz. A controller can also be used to adjust the amplitude and frequency for a particular application. In an alternative embodiment, an AC line source of any origin can be used. The AC source is converted to any desired frequency range, such as from about one (1) Hz to 50 kHz. The magnitude and frequency of the oscillations can also be controlled for a particular application.

In the embodiment shown in FIG. 1A, a source of air power is used to activate the motor 106. Specifically, when the power adjustment switch 118 is activated, a supply of air (not shown) is drawn into the turbine 111 through the air connector 116. The rotating motion of the turbine components is transmitted through the turbine-generator connector 109 to the generator 112. The generator 112 converts this mechanical energy into electrical energy and sends the appropriate signal through the generator-electronics connector 113 to the drive electronics 114, which in turn activates the motor 106 via the electronics-motor connector 115. Conventional connections, such as tubing and wiring, which are well known in the art are used for the various connectors (109, 113, 115 and 116) described herein. The power adjustment switch 118 can be a simple on/off switch. In an alternative embodiment, the power switch 118 is a dial switch. In this embodiment, a range of power output is possible, so that the output (such as the amplitude of vibration) can be set at the appropriate level for a particular application and so that the power level can be adjusted as needed during a particular application.

In operation, the user places the tool insert 104 into the magnetic insert (122*a* or 122*b*), which is in turn threaded to the wave guide 108. Alternatively, the tool insert 104 can be attached directly to the wave guide 108 if both components are sufficiently magnetic. In the embodiment shown in FIG. 1A, the open-ended magnetic insert 122*a* has already been threaded into the wave guide 108 as described. When the power adjustment switch 118 is turned on, power is provided to the motor 106 as described above. Once the motor 106 is activated, energy from the motor 106 is transmitted to the magnetic coupling system 110*a* to create a magnetic field around the permanent magnet 120. The magnetic field provided by the permanent magnet 120 can clamp the two mating parts (wave guide 108 and tool insert 104) together with up to about 17.8 Newtons (N) (about four (4) lbf) or more of force. The energy from the motor 106 is further transferred across the magnetic coupling system 110*a* from the wave guide 108 to the tool insert 104. In the embodiment shown in FIG. 1A, ultrasonic energy in the form of vibrations 124 are transferred across the magnetic coupling system 110*a*. At this point, the user can then use the device to perform the desired function, such as cleaning calculus from teeth, and so forth. The tool insert 104 is removable by firmly pulling the tool insert 104 away from the wave guide 108, preferably after the power is turned off.

Figure 6:
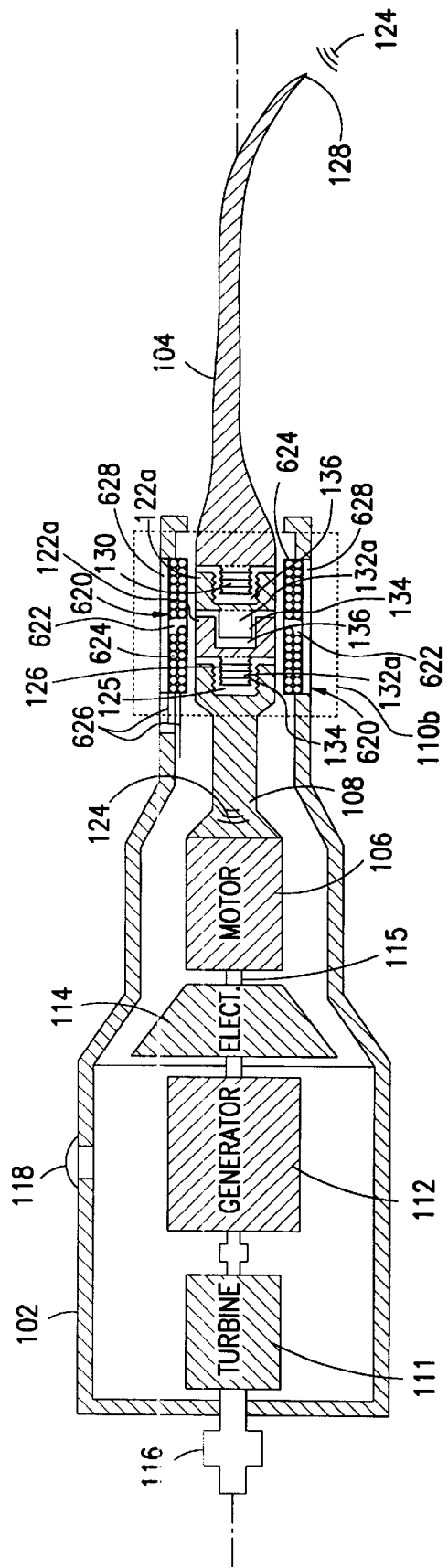
FIG. 6 is a cross-sectional partially expanded view of a dental tool with an alternative magnetic coupling system having an electromagnet in one embodiment of the present invention.

FIG. 6 shows a cross-sectional view of one embodiment of the present invention comprising an alternative magnetic coupling system 110b. The handpiece 102 contains the motor 106, wave guide 108, alternative magnetic coupling system 110b, turbine 111, generator 112 and electronics 114 as described above. The alternative magnetic coupling system 110b uses an electromagnet 620 rather than the permanent magnet 120 used in the magnetic coupling system 110a. The alternative magnetic coupling system 110b shown in FIG. 6 shows two open-ended magnetic inserts 122a. The use of two open-ended magnetic inserts 122a is for exemplary purposes only, as it is also possible to use only one open-ended magnetic insert 122a (or one dual-stubbed magnetic insert 122b), or any other type and number of magnetic inserts, depending on the particular application and type of materials, as discussed above. Specifically, two magnetic inserts can be used when neither of the mating parts, i.e., the wave guide 108 nor the tool insert 104, are magnetic or are otherwise weakly magnetic, such as paramagnetic materials or possibly diamagnetic materials. Otherwise, if one of the mating parts is sufficiently magnetic, only one magnetic insert needs to be used as in FIG. 1A.

The electromagnet 620 in the alternative magnetic coupling system 110b comprises an internal magnetic bobbin 622, a coil wire 624 having lead wires 626, and an external magnetic bobbin 628. (For clarity, the components of the alternative magnetic coupling system 110b are shown in a partially expanded view so that they appear separated, although in use, the wave guide, the open-ended magnetic inserts 122a and the tool insert 104 are all in direct contact as in previously described embodiments). The coil wire 624 is wrapped around the internal magnetic bobbin 622 such that the lead wires 626 extend past the end of the internal magnetic bobbin 622 as shown. In the embodiment shown in FIG. 6, there are two windings of the coil wire 624 and the two lead wires 626 extend out from the same end of the internal magnetic bobbin 822. In an alternative embodiment, any number of windings can be used and the lead wires 626 can extend out from any portion of the internal magnetic bobbin 622. The external magnetic bobbin 628 provides a "covering" for the coil wire 624 and functions to increase the magnetic flux density. In an alternative embodiment, there is no external magnetic bobbin 628.

In the embodiment shown in FIG. 6, there is one electromagnet 620 surrounding the open-ended magnetic inserts 122a. The electromagnet 620 is lodged inside the handpiece 102 in any suitable manner, such as the various ways in which the permanent magnet 120 in FIG. 1A can be embedded in the handpiece 102.

The internal and external magnetic bobbins, 622 and 628, respectively, can be any suitable size and can be made from any suitable magnetic material as is known in the art for electromagnets, including all of the magnetic materials described herein. In one embodiment, the internal and external magnetic bobbins, 622 and 628, respectively, are about one (1) to ten (10) cm (about 0.4 to four (4) in) in length and about one (1) to ten (10) cm (about 0.4 to four (4) in) in diameter.

The wire coil 624 can be made from any suitable electrically conductive material as is known in the art, including, but not limited to copper, silver and aluminum. The size of the wire coil 624 depends on the particular application. Generally, for hand held tools, a smaller size may be desirable, so that the wire is not too large or heavy. In one embodiment, the wire coil 624 is about 16 American Wire Gauge (AWG) to about 36 AWG. In another embodiment, the wire coil 624 is about 12–15 AWG or less.

As with the open-ended magnetic insert 122a in FIG. 1A that couples with the wave guide 108, the open-ended magnetic insert 122a in FIG. 6 that couples with the wave guide 108 can have suitable threads 134 on its magnetic insert stub 132a so that it can be screwed into the wave guide 108. Similarly, the magnetic insert cavity 136 associated with this open-ended magnetic insert 122a has no threads, nor does the magnetic insert stub 132a of the adjacent open-ended magnetic insert 122a, because these two components are not screwed together, but instead are inserted together. In this way, the magnetic coupling system 110b (or 110a) is used to enhance a raw connection with magnetics, i.e., the magnetic coupling system 110b, rather than merely being used to enhance a threaded connection. This adjacent open-ended magnetic insert 122a shown in FIG. 6 is threaded to the tool insert 104 via threads on the tool insert stub 130 and threads surrounding the circumference of the magnetic insert cavity 136. In an alternative embodiment, the two open-ended magnetic inserts 122a are threaded together, with the connection being enhanced by magnetics. Other alternative embodiments include press fitting one of the open-ended magnetic inserts 122a into the wave guide cavity 125 and/or press fitting one open-ended magnetic insert 122a into an adjacent magnetic insert 122a. In another alternative embodiment, at least one of the magnetic inserts is dual-stubbed as shown in FIG. 2. In yet another alternative embodiment, one of the magnetic inserts is essentially dual-stubbed, but has only a small protrusion or extension on one end which fits or slips into a corresponding cavity of the adjacent magnetic insert without threads.

The open-ended magnetic inserts 122a in FIG. 6 are arranged to exert a magnetic attraction force for one another. It is known that magnetic field strength is directly proportional to the size of the current. In this way, when current is applied to the lead wires 626, a strong magnetic field is created between the open-ended magnetic inserts 122a. The current also causes a strong magnetic field to be created around the electromagnet 620, which surrounds the open-ended magnetic inserts 122a. This causes the two mating parts (wave guide 108 and tool insert 104) to be magnetically attracted together. Any suitable current can be used. In one embodiment, the current is about 50 milliamps (mA) to about ten (10) amps (A), depending on the size of the wire.

Figure 7:
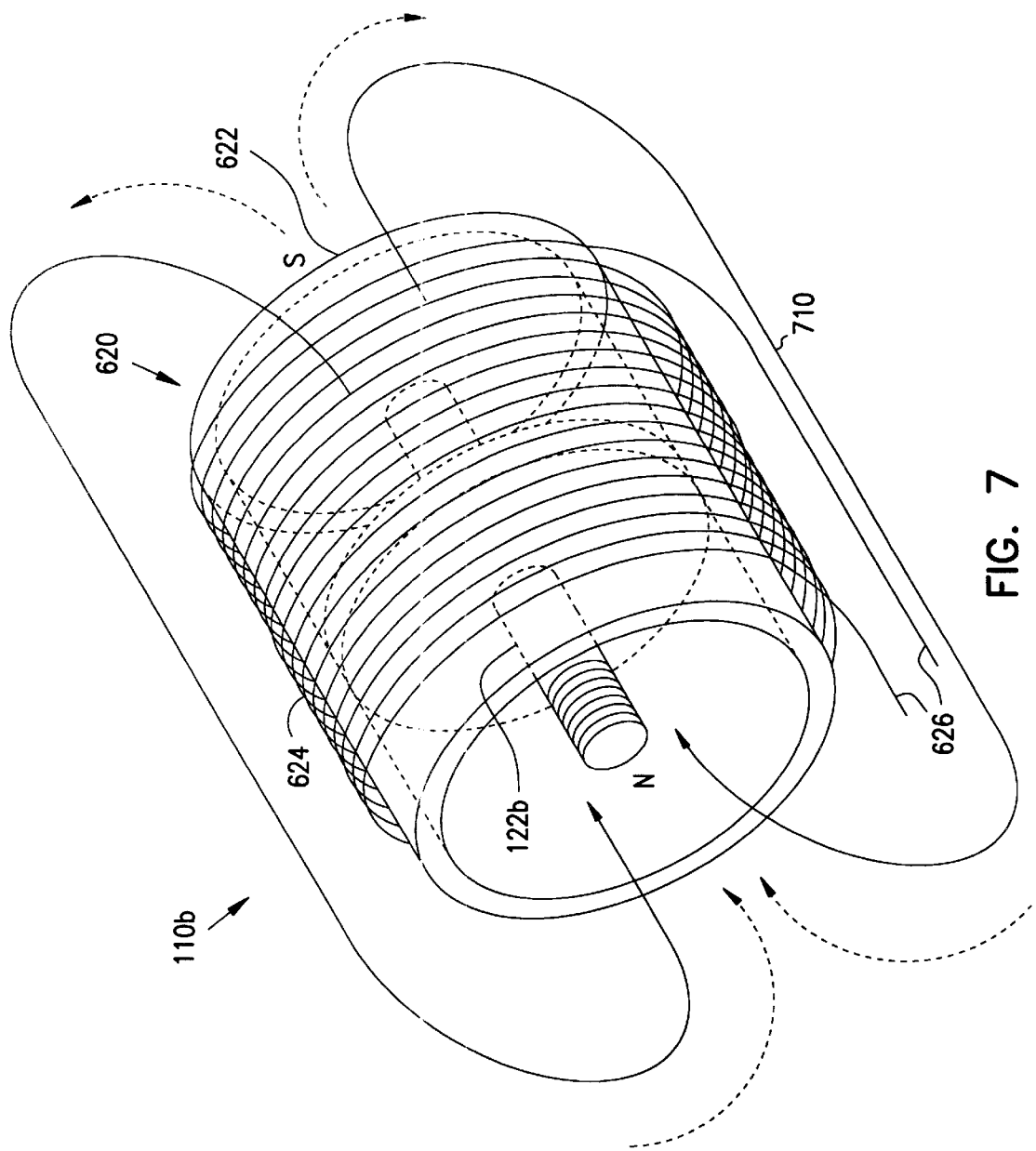
FIG. 7 is a simplified perspective illustration of the alternative magnetic coupling system shown in FIG. 6 with the corresponding flux lines showing axial polarization.

FIG. 7 shows a perspective view of the electromagnet 620 without an external magnetic bobbin 628, surrounding a dual-stubbed magnetic insert 122b. Since the wire coil 624 can only produce axial magnetic flux, the electromagnet 620 can only be magnetized in the axial direction, similar to the permanent magnet 120 shown in FIG. 5B. This is indicated by the flux vectors 710 as shown in FIG. 7. Again, although the poles and orientation of the dual-stubbed magnetic insert 122b is not noted on FIG. 7 it can be assumed that the dual-stubbed magnetic insert 122b is aligned such that it exerts a magnetic attraction at each end for each of the mating parts being combined.

In operation, when there is no current being applied to the wire coil 624, a user can place the tool insert 104, such as a dental scaler, onto the wave guide 108. Once the tool insert 104 is in place, the wire coil 624 can be energized by moving the power adjustment switch 118 to the "on" position as described above. The magnetic field created by the wire coil 624 induces a strong magnetic field between the magnetic inserts as noted above. In one embodiment, the magnetic field can produce as much as about 22.3 N (five (5) lbf) or more of attraction force securing the components to each other with small amounts of power. The attraction force can be determined according to mathematical relationships well known in the art and discussed in Moskowitz, supra. The power consumption required to produce this force will vary depending on several factors known in the art, including the amount of air in the magnetic circuit. In one embodiment, the power required is about five (5) to 15 watts or more. In an alternative embodiment, the power required is less than about three (3) watts of power. In another alternative embodiment, the diameter of the internal magnetic bobbin 622 is about five (5) to about 7.6 cm (about two (2) to about three (3) in). In this embodiment, the magnetic field can produce as much as about 3,234 N (725 lbf) or more of attraction force with an input power of up to about 500 watts or more.

Figure 8:
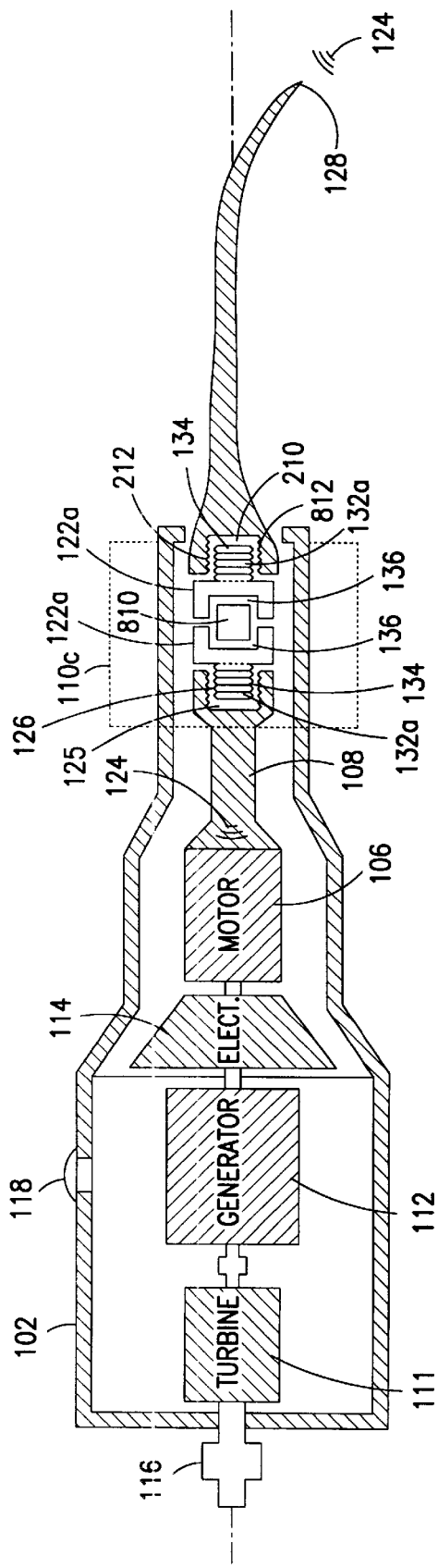
FIG. 8 is a cross-sectional partially expanded view of a dental tool with another alternative magnetic coupling system having a permanent magnet located between two magnetic inserts in one embodiment of the present invention.

The connector scheme shown in FIG. 8 uses a passive magnetic coupling system 110c to couple the wave guide 108 to the tool insert 104. (Again, for clarity, the components of the passive magnetic coupling system 110c are shown in a partially expanded view so that they appear separated, although in use, the wave guide, the open-ended magnetic inserts 122a and the tool insert 104 are all in direct contact as in previously described embodiments). The handpiece 102 shown in FIG. 8 contains the motor 106, wave guide 108, turbine 111, generator 112 and electronics 114 as described above. In the embodiment shown in FIG. 8, however, the handpiece 102 contains a passive magnetic coupling system 110c which comprises two open-ended magnetic inserts 122a and a high power magnet 810, all of which are magnetized prior to being placed in the magnetic circuit. Firm connection occurs when the tool insert 104 is inserted over the high power permanent magnet 810. The magnetic field can clamp the two mating parts (wave guide 108 and tool insert 104) together with up to about 17.8 N (about four (4) lbf) or more of force. The tool insert is modified as in FIG. 2 to have a tool insert cavity 210. Additionally, in the embodiment shown in FIG. 8, the tool insert cavity 210 has threads 812. The tool insert 104 is removable by firmly pulling the tool insert 104 away from the wave guide 108. In an alternative embodiment, there are no threads on the magnetic insert stubs 134a, and the components are inserted together, with the raw connection being enhanced by magnetics, i.e., the magnetic coupling system 110c, as described above.

The high power magnet 810 is positioned in a cavity created by the two open-ended magnetic inserts 122a, each having a cavity 136, as described above in FIGS. 1A and 1B and shown in FIG. 8. In one embodiment, one or both of the cavities 136 are modified to be larger than the cavity 136 in the open-ended magnetic inserts 122a described above. Specifically, the cavities 136 can be of any suitable size and shape, and are located opposite the magnetic insert stubs 132, i.e., opposite the ends which connect with the two mating parts. Placing two cavities 136 together in this manner provides the space for the high power magnet 810. The high power magnet 810 is a permanent magnet having remanent magnetic field values greater than about 2500 gauss.

Figure 9:
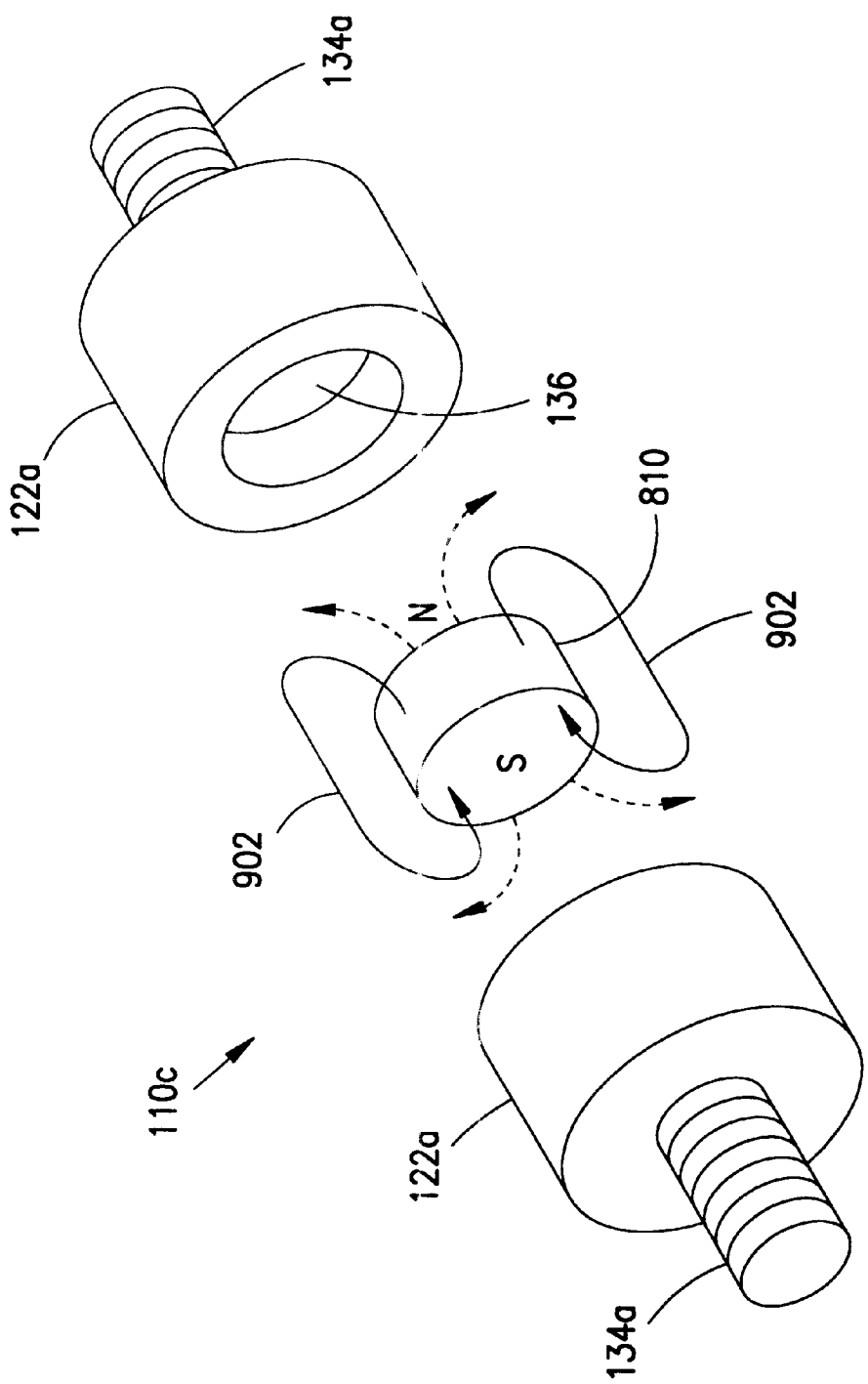
FIG. 9 is an exploded view of the alternative magnetic coupling system shown in FIG. 8 with the corresponding flux lines showing axial polarization.

FIG. 9 shows an exploded view of the passive magnetic coupling system 110c comprising the high power magnet 810 between the two open-ended magnetic inserts 122a. The poles of the high power magnet 810 are indicated by "N" and "S." The high power magnet 810 exerts an attraction force for both of the open-ended magnetic inserts 122a. Further, it can be assumed in this embodiment that the open-ended magnetic inserts 122a are axially aligned and that each exert an attraction force for the component to which it attaches. Flux lines 902 exit the high power magnet 810 as shown, such that the flux is parallel to the axis of the high power magnet 810, and is not directed radially inward. The high power magnet 810 can be any suitable shape, such as square, rectangular, barrel or elliptical. In one embodiment the high power magnet 810 is circular. In another embodiment a Cast Alnico 57 magnet having a residual induction (Br) of 13,500 gauss made by Crucible Magnetics in Elizabethtown, Ky. is used.

The present invention is also directed to a method of releasably coupling a tool insert, such as a dental scaler insert, by using a magnetic coupling interface. The method includes the use of a magnetic coupling system as described above, and includes the steps of inserting a tool insert onto a magnetic insert and causing the magnetic insert to indirectly or directly contact a cavity in a wave guide. In an alternative embodiment, there is no wave guide, and contact is made directly or indirectly with a motor, such as an ultrasonic motor. The method further includes activating a permanent magnet or electromagnet located proximate to the magnetic insert in order to provide a magnetic coupling between the wave guide and tool insert.

In addition to providing a method for releasably connecting two mating parts, the magnetic coupling systems of the present invention also transmit energy from one component to another. In one embodiment, ultrasonic energy is transferred to the tool insert 104, thus causing the tip 128 to vibrate as discussed above in relation to FIGS. 1A, 6 and 8. Any suitable amount of magnetic force or pressure can be used to hold the mating parts together, depending on the application. In one embodiment, the stress at the magnetic attachment plane is about 0.69 MPa (about 100 psi). This corresponds to a force of about 22.3 N (five (5) lbf) such that the magnetic attraction force at the magnetic attachment plane is greater than 22.3 N (five (5) lbf), such as about 27.7 N (about six (6) lbf). As a result, the components of the magnetic coupling system stay in contact, thus allowing for efficient transmission of vibration through coupling. In an alternative embodiment, the magnetic assembly holds two components together with a force of about 10 N (about 2.2 lbf). In another alternative embodiment, the components are held together with a force of about 600 N (about 135 lbf).

Figure 10:
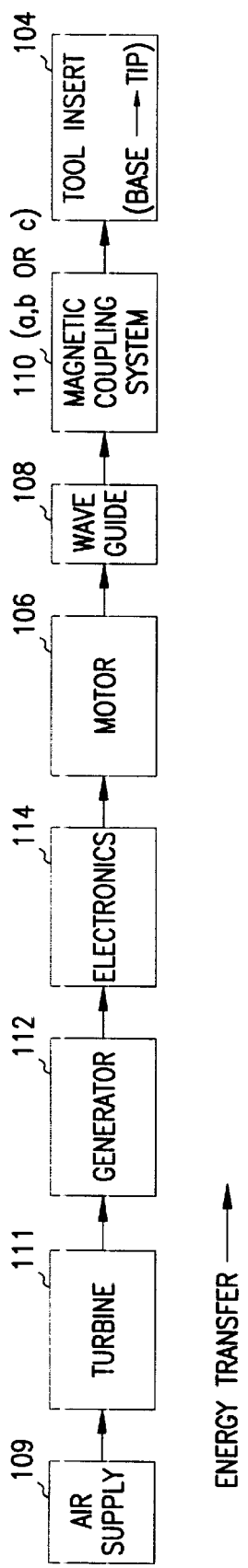
FIG. 10 is a flow diagram showing components through which energy can be transferred in one embodiment of the present invention.

FIG. 10 is a system drawing showing the components through which energy is transferred. This includes the air supply 109, turbine 111, generator 112, electronics 114, motor 106, wave guide 108, magnetic coupling system 110(a, b or c) and tool insert 104 discussed herein. Any conventional turbine 111 can be used in this invention, such as a conventional air turbine. The turbine 111 can have performance characteristics suitable for the particular application. It is known that turbine shaft output is dependent on turbine efficiency. In one embodiment, the input air supply power is about 60 to about 90 watts. In another embodiment, the air turbine 111 is any type of conventional turbine well known in the dental field having a power output of about ten (10) to about 50 watts. In a particular embodiment, an RDH vane motor made by Midwest Dental, Inc., in Des Plaines, Ill., is used. The air supply 509 connected to the turbine 111 can be at any suitable pressure, such as about 0.28 to 0.345 MPa (about 40 to 50 psi).

Any conventional generator 112 can be used, such as a DC generator. The generator 112 preferably has performance characteristics suitable for a particular application. Both the turbine 111 and generator 112 are designed to be capable of producing sufficient power output for the particular motor 106 being used.

The electronics 114 can comprise conventional drive electronics known in the art. The electronics 114 are used to power the motor 106 using the DC voltage supplied by the turbine 111 and generator 112. In one embodiment about 25 to about 40 kHz of DC power is provided. A potentiometer can also be used to regulate or adjust the power which is output from the generator 112 to the electronics 114. In one embodiment, the system utilizes open loop control with variable gain used to regulate the electronics 114.

Regarding testing and analysis of the magnetic coupling system, modal analysis is a well-known method for providing information on the manner in which objects vibrate. By performing modal analysis, it is possible to determine a preferred coupling system location which will require a minimum amount of pressure to hold the mating parts together. If the magnetic coupling system does not have adequate attraction, the existing stress or pressure of the vibration will cause the tool insert to detach from the wave guide. Modal analysis involves determination of the relationship between the velocity and pressure of the system. An "antinode" is a location of zero pressure and maximum velocity. A "node" is a location of maximum pressure or stress and zero velocity. In actual applications, the antinode and node may not be precisely defined, such that there may exist a small amount of pressure at the antinode and some velocity at the node.

In one embodiment, the stress state near the anti-node, or point of coupling, is sufficiently low so that magnetic coupling is feasible. Additional modal analysis will be used to optimize the system and ensure that adequate attraction is provided.

Testing will be performed using a hand held dental scaler to determine performance characteristics of the various system components. Turbine, generator, electronics and motor designs will be integrated together, and the system will be tested to determine various performance characteristics such as resonant frequency, ultrasonic motor transfer function, generator power, ultrasonic motor power input, and so forth. Magnetic, mechanical and dynamic analysis will be performed to design a tip for optimum elastic wave energy transmission.

Air turbine performance characteristics of various Midwest Dental air turbines and turbines produced by other manufacturers will be reviewed. In order to complete this testing, power curves showing torque vs. rpm will be used for each particular turbine.

Various off-the-shelf generators will be tested. A DC motor may also be used to simulate the operation of a generator by running it backwards. The best performing generators and turbines will be tested together to determine output power capability. The requisite air supply and tubing for this testing will be supplied by Dentsply of York, Pa. Compatibility of the turbine/generator power output capability and estimated power requirements of a 25 kHz ultrasonic motor (and likely other ultrasonic motors), will be evaluated.

Drive electronics will be designed to power a selected ultrasonic motor using the DC voltage supplied by the turbine/generator. Electronics design schematics will be based on previously known battery-operated systems.

A suitable ultrasonic motor will be developed. This may be a 25 kHz motor, a 30 kHz motor, or a motor having some other suitable frequency. For a 25 kHz motor, such design and development will begin with a 25 kHz tip design and dimensional information supplied by the maker of the tool insert to be used. For the 25 kHz motor, it is likely a 25 kHz Dentsply dental tip will be tested. In this way the motor will be designed as a system including tip dynamic effects. It is possible that other ultrasonic motors designed for having different tip dynamic effects will be developed and tested as well. Magnetic, mechanical, electrical as well as modal analyses will be performed to maximize device efficiency and ensure compatibility with the selected power generator.

CONCLUSION

Magnetic coupling of components, whether at ultrasonic or sonic frequencies, can be used in a variety of applications. Some areas of use include, but are not limited to, the coupling of components in high power ultrasonic sonochemical applications, sonic and ultrasonic knife blades for the enhancement of cutting, coupling of acoustic elements between motor and loud speakers or warning systems, the connection of ultrasonic surgical motors to surgery implements, and so forth.

The magnetic coupling system gives the user the ability to quickly remove and attach implements. The method is cost effective because it is no longer necessary to discard an entire motor when a tool insert needs replacement. Furthermore, the method is relatively simple and inherently gives devices longer reliability than devices coupled using conventional methods, because problems such as galling and thread wear are not present. Those skilled in the art will recognize that the magnetic interface described herein can be used in any suitable system which comprises the necessary mechanical and electrical components, as well as a suitable type of system controller, if applicable.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is manifestly intended that this invention be limited only by the claims and the equivalents thereof.

What is claimed is:

1. A magnetic coupling system comprising a magnetic assembly having one or more permanent magnets or an electromagnet located proximate to coupling ends of a base structure and tool insert, the magnetic assembly designed to removably combine the base structure and tool insert, wherein the base structure has a transducer which provides vibrational motion that can be transmitted through the magnetic assembly directly to the tool insert.

2. The system as recited in claim 1 wherein the vibrational motion in the base structure is transformed to elliptical or flexural motion in the tool insert.

3. The system as recited in claim 1 wherein the magnetic assembly can hold the base structure and tool insert together with a force of about ten (10) to about 600 Newtons.

4. The system as recited in claim 1 wherein the transducer is an ultrasonic motor, further wherein ultrasonic energy is passed from a wave guide in direct contact with the motor to the tool insert.

5. The system as recited in claim 4 wherein the tool insert is an ultrasonic dental scaling tool.

6. The system as recited in claim 5 wherein the wave guide is made from titanium and the tool insert is made from steel.

7. The system as recited in claim 4 wherein the ultrasonic motor operates at frequencies between about 18 kHz and 40 kHz.

8. The system as recited in claim 1 wherein the transducer is a sonic motor operating at frequencies less than about 18 kHz, further wherein sonic energy is passed from a wave guide in direct contact with the motor to a tool insert.

9. The system as recited in claim 1 wherein power means provide power to the transducer through electronics connected to the transducer.

10. The system as recited in claim 1 wherein the magnetic assembly further comprises one or more magnetic inserts located between the base structure and tool insert, further wherein one or both of the base structure and tool insert are non-magnetic, paramagnetic or diamagnetic.

11. The system as recited in claim 10 wherein the one or more permanent magnets surround the one or more magnetic inserts.

12. The system as recited in claim 11 wherein the one or more permanent magnets are radially polarized, axially polarized, or polarized at an intermediate angle.

13. The system as recited in claim 10 wherein the permanent magnet is placed between two magnetic inserts.

14. The system as recited in claim 10 wherein the electromagnet surrounds the one or more magnetic inserts.

15. The system as recited in claim 10 wherein the one or more magnetic inserts are made from soft or hard ferromagnetic material.

16. The system as recited in claim 15 wherein the ferromagnetic material is selected from the group consisting of iron, steel, nickel, cobalt, alnico, permalloy, barium oxide and strontium oxide.

17. The apparatus as recited in claim 10 wherein the permanent magnet surrounds the one or more magnetic inserts and is radially polarized, axially polarized or polarized at an intermediate angle.

18. The system as recited in claim 11 wherein the one or more magnetic inserts are open-ended, dual-stubbed or a combination thereof.

19. The system as recited in claim 18 wherein at least one of the one or more magnetic inserts is threaded.

20. An apparatus comprising a passive magnetic coupling system having an ultrasonic transducer adapted to couple with a tool insert, the transducer having a permanent magnet with a remanent magnetic field value greater than about 2500 gauss, the permanent magnet located between two magnetic inserts and designed to magnetically attract the transducer and tool insert together, wherein the permanent magnet and magnetic inserts are magnetized prior to placement in a magnetic circuit, further wherein vibrational energy is transferred from the transducer to the tool insert.

21. The apparatus as recited in claim 20 wherein the magnetic inserts are open-ended.

22. The apparatus as recited in claim 20 wherein the transducer is an ultrasonic motor operating at frequencies between about 18 kHz and 40 kHz, further wherein a wave guide is located between the transducer and the tool insert.

23. The apparatus as recited in claim 22 wherein the wave guide is made from a nonmagnetic material and the one or magnetic inserts are made from iron, steel, nickel, cobalt, alnico, permalloy, barium oxide or strontium oxide.

24. A method for removably coupling a base structure and tool insert together, comprising:
  connecting the base structure and tool insert together;
  applying a magnetic field to the base structure and tool insert by activating a transducer located in the base structure using power from a power source, the magnetic field produced with a magnetic assembly comprising one or more permanent magnets or an electromagnet located proximate to coupling ends of the base structure and tool insert; and
  transferring vibrational energy from the transducer across the magnetic assembly directly to the tool insert.

25. The method as recited in claim 24 wherein the magnetic assembly holds the base structure and tool insert together with a force of about ten (10) to about 600 Newtons.

26. The method as recited in claim 24 wherein the transducer is an ultrasonic motor, further wherein ultrasonic energy is passed from a wave guide in direct contact with the motor to the tool insert.

27. The method as recited in claim 26 further comprising transforming vibrational motion in the base structure to elliptical or flexural motion in the tool insert.

28. The method as recited in claim 27 wherein the tool insert is an ultrasonic dental scaling tool.

29. The method as recited in claim 28 wherein the ultrasonic motor operates at frequencies between about 18 kHz and 40 kHz.

30. The method as recited in claim 24 wherein the transducer is a sonic motor operating at frequencies less than about 18 kHz, further wherein sonic energy is passed from a wave guide in direct contact with the motor to the tool insert.

31. The method as recited in claim 24 wherein the one or more permanent magnets are placed between two magnetic inserts and have remanent magnetic field values greater than about 2500 gauss.

32. The method as recited in claim 24 wherein the electromagnet surrounds the one or more magnetic inserts.

33. The method as recited in claim 24 wherein the one or more permanent magnets surround the coupling ends of the base structure and tool insert.

34. The method as recited in claim 24 wherein one or both of the base structure and tool insert are non-magnetic, further wherein the magnetic assembly also comprises one or more magnetic inserts located between the two components.

35. The method as recited in claim 34 wherein the permanent magnet surrounds the one or more magnetic inserts.

36. The method as recited in claim 35 wherein the permanent magnet is radially polarized, axially polarized or polarized at an intermediate angle.

37. The method as recited in claim 36 wherein the one or more magnetic inserts are made from soft or hard ferromagnetic material.

38. The method as recited in claim 37 wherein the ferromagnetic material is selected from the group consisting of iron, steel, nickel, cobalt, alnico, permalloy, barium oxide and strontium oxide.

39. The method as recited in claim 37 wherein the transducer is an ultrasonic motor, further wherein ultrasonic energy is passed from a wave guide in direct contact with the motor to the tool insert.

40. The method as recited in claim 39 wherein the tool insert is an ultrasonic dental scaling tool.

41. The method as recited in claim 40 wherein the ultrasonic motor operates at frequencies between about 18 kHz and 40 kHz.

42. An apparatus for coupling two components comprising:
  means for applying a magnetic field to the two components, wherein the two components are a wave guide and a tool insert;
  means for coupling the wave guide and tool insert with the magnetic field; and
  means for transferring sound waves directly from the waveguide to the tool insert, wherein the sound waves cause the tool insert to vibrate.

43. The apparatus as recited in claim 42 wherein the means for applying the magnetic field is a motor having a drive rod made from a material selected from the group consisting of magnetostrictive, piezoelectric and piezoceramic materials.

44. The apparatus as recited in claim 43 wherein the magnetostrictive material is Terfenol or Terfenol-D.

45. The apparatus as recited in claim 43 wherein the motor has a frequency output greater than about 18 kHz and a power output of about 5.8 to six (6) watts.

46. The apparatus as recited in claim 45 wherein the motor has no separate cooling fixtures.

47. The apparatus as recited in claim 46 wherein the means for coupling and the means for transferring sound waves is a magnetic coupling system, further wherein torque is not transmitted by the magnetic coupling system to the tool insert.

48. The apparatus as recited in claim 47 wherein the magnetic coupling system is one or more permanent magnets or an electromagnet.

49. The apparatus as recited in claim 48 wherein one or both of the two components are non-magnetic, paramagnetic or diamagnetic, further wherein one or more magnetic inserts are used between the two components.

50. A magnetic assembly having one or more permanent magnets or an electromagnet located proximate to coupling ends of a base structure and a tool insert, the magnetic assembly designed to removably combine the base structure and tool insert, wherein the base structure has an ultrasonic motor capable of operating at frequencies between about 18 kHz and 40 kHz, the ultrasonic motor further having a titanium wave guide in direct contact with the magnetic assembly, wherein the ultrasonic motor provides vibrational energy that can be transmitted through the wave guide and magnetic assembly directly to the tool insert where it is transformed to elliptical or flexural motion.

51. The method as recited in claim 50 wherein the wave guide is about ¼ the length of the tool insert and the displacement amplitude at the tip of the tool insert is about 100 microns peak-to-peak.

* * * * *

UNITED STATES PATENT AND TRADEMARK OFFICE
CERTIFICATE OF CORRECTION

PATENT NO. : 6,227,853 B1
DATED : May 8, 2001
INVENTOR(S) : Thomas T. Hansen and Billy R. Flowers It is certified that error appears in the above-identified patent and that said Letters Patent is hereby corrected as shown below:

Column 19,
Line 26, delete "apparatus" and insert -- system --, therefor.
Line 27, delete "permanent magnet surrounds" and insert -- the one or more permanent magnets surround --, therefor.
Line 28, delete "is" and insert -- are --, therefor.
Line 30, delete "claim 11" and insert -- claim 10 --, therefor.
Line 53, insert -- more -- between "one or" and "magnetic".

Column 20,
Line 52, delete "18." and insert -- 18 --, therefor.

Signed and Sealed this

Twenty-third Day of April, 2002

Attest:

Attesting Officer

JAMES E. ROGAN
Director of the United States Patent and Trademark Office